(12) United States Patent
Wilkins (10) Patent No.: US 9,194,794 B2
(45) Date of Patent: Nov. 24, 2015

(54) OPTICAL ABSORPTION SPECTROSCOPY

(75) Inventor: Steven Wilkins, Bristol (GB)

(73) Assignee: DUVAS TECHNOLOGIES LIMITED, London (GB)

(*) Notice: Subject to any disclaimer, the term of this patent is extended or adjusted under 35 U.S.C. 154(b) by 197 days.

(21) Appl. No.: 13/700,633

(22) PCT Filed: Jun. 2, 2011

(86) PCT No.: PCT/GB2011/000842
§ 371 (c)(1), (2), (4) Date: Mar. 6, 2013

(87) PCT Pub. No.: WO2011/151629
PCT Pub. Date: Dec. 8, 2011

(65) Prior Publication Data
US 2013/0188170 A1    Jul. 25, 2013

(30) Foreign Application Priority Data
Jun. 3, 2010   (GB) .................................. 1009327.6

(51) Int. Cl.
*G01N 21/00*   (2006.01)
*G01N 21/25*   (2006.01)
*G01N 21/33*   (2006.01)
*G01N 21/3504*   (2014.01)
(Continued)

(52) U.S. Cl.
CPC ............ *G01N 21/255* (2013.01); *G01N 21/031* (2013.01); *G01N 21/31* (2013.01); *G01N 21/33* (2013.01); *G01N 21/3504* (2013.01); *G01N 21/3577* (2013.01); *G01N 21/0303* (2013.01); *G01N 2021/3155* (2013.01); *G01N 2201/0668* (2013.01)

(58) Field of Classification Search
CPC .............. G01N 21/00; G01N 21/0303; G01N 2021/3155
USPC .......................................................... 356/436
See application file for complete search history.

(56) References Cited

U.S. PATENT DOCUMENTS 4,291,988 A * 9/1981 Dixon et al. ................... 356/437
4,455,376 A   6/1984 Maines
(Continued)

FOREIGN PATENT DOCUMENTS

| EP | 0 457 624 A1 | 11/1991 |
| EP | 0 457 624 B1 | 10/1995 |
| WO | WO 03/078974 | 9/2003 |

OTHER PUBLICATIONS

British Search Report dated Oct. 13, 2010 for Application No. GB1009327.6.
(Continued)

*Primary Examiner* — Roy M Punnoose
(74) *Attorney, Agent, or Firm* — Foley & Lardner LLP; Christopher J. McKenna (57) ABSTRACT

An optical absorption spectroscopy apparatus comprises a multi-pass optical cell (1) having a first reflector (2) and a second reflector (4, 4'), a first light source (6) for light of a first waveband and a second light source (6') for light of a second waveband. The cell (1) is constructed and arranged such that light entering the cell is reflected one or more times between the first and second reflectors (2, 4, 4') before exiting the cell. Light of the first waveband enters and exits the cell (1) in a first plane and light of the second waveband enters and exits the cell in a second plane that is different from the first plane.

19 Claims, 7 Drawing Sheets

(51) Int. Cl.
    *G01N 21/3577*    (2014.01)
    *G01N 21/03*    (2006.01)
    *G01N 21/31*    (2006.01)

(56) References Cited

U.S. PATENT DOCUMENTS

| | | |
|---|---|---|
| 4,749,276 A | 6/1988 | Bragg et al. |
| 4,969,156 A | 11/1990 | Schiller et al. |
| 5,440,143 A | 8/1995 | Carangelo et al. |
| 5,444,528 A * | 8/1995 | Puschell .......................... 356/73 |
| 5,726,752 A * | 3/1998 | Uno et al. ..................... 356/246 |
| 5,734,165 A | 3/1998 | Unal et al. |
| 5,838,008 A | 11/1998 | Esler et al. |
| 5,867,329 A | 2/1999 | Justus et al. |
| 6,404,501 B1 | 6/2002 | Hafeman et al. |
| 6,611,333 B1 * | 8/2003 | Uehara et al. ................. 356/432 |
| 6,748,334 B1 * | 6/2004 | Perez et al. .................... 702/24 |
| 6,937,341 B1 | 8/2005 | Woollam et al. |
| 7,288,770 B2 * | 10/2007 | Gamiles et al. ................ 250/372 |
| 8,299,433 B2 * | 10/2012 | Majewski et al. .......... 250/338.1 |
| 2003/0134427 A1 * | 7/2003 | Roller et al. .................. 436/171 |
| 2007/0081162 A1 * | 4/2007 | Roller et al. .................. 356/437 |
| 2007/0182965 A1 * | 8/2007 | Kamlet et al. ................. 356/437 |
| 2013/0003045 A1 * | 1/2013 | Wilkins .......................... 356/51 |

OTHER PUBLICATIONS

International Search Report dated Oct. 4, 2011 for International application No. PCT/GB2011/000842.

White, John U., "Long Optical Paths of Large Aperture", Journal of the Optical Society of America, vol. 32, pp. 285-288, May 1942.

Uehara, K. et al., "Isotope analysis of environmental substances by a new laser-spectroscopic method utilizing different pathlengths", Elsevier, Sensors and Actuators, B 74 (2001) pp. 173-178.

White cell (spectroscopy), Wikipedia printed Jul. 14, 2011, 1 page.

* cited by examiner

The reflectance of various films of silver, gold, aluminium, copper, rhodium and titanium Ref: W.M. Rohsenow and H. Choi, Heat Mass and Momentum Transfer, Prentice Hall, New York, (1961)

Polycrystalline IR (PIR) transmission in far-IR spectrum [ref Fibre Photonics]

OPTICAL ABSORPTION SPECTROSCOPY

FIELD

The present invention relates to an apparatus for optical absorption spectroscopy and a method of optical absorption spectroscopy. In particular, but not exclusively, the invention relates to apparatus and methods for detecting the presence and/or concentration of one or more substances by measuring the absorption of one or more different wavebands of light, by differential or conventional optical absorption spectroscopy. The detected substances may be fluids (gases or liquids), for example pollutants or hazardous substances.

BACKGROUND

The concentration of one or more fluid substances (i.e. gases or liquids) within a sample can be determined via optical absorption spectroscopy, by passing light through the sample and detecting the optical absorption characteristics of those substances. The term "light" as used herein is intended to encompass the infrared and ultraviolet wavebands, as well as visible light. The term "waveband" refers to each of the three broad spectra of light comprising ultraviolet, visible and infrared light having frequency ranges respectively of 30000-790 THz, 790-400 THz and 400-0.3 THz, and also to subdivisions of those spectra such as the near infrared (400-120 THz).

The amount of light absorbed by the substance and therefore the sensitivity of the method depends on the concentration of the substance and the path length of light through the substance. In gases, the concentration in terms of molecules per unit volume is generally much lower than in liquids or solids and therefore the path length of the light through the sample must be correspondingly higher. For example, the required path length is typically between about 2 m and 100 m for gas mixtures containing low concentrations of the target gases, such as atmospheric pollutants. This large path length can be achieved either by placing the light source and the detector far apart or by reflecting the light backwards and forwards through a sample in an optical cell so that it passes through the sample numerous times before reaching the detector.

The utilisation of a multi-pass optical cell can therefore provide a long path length in an apparatus having a compact form. An example of a multi-pass optical cell is the White cell. The basic White cell is a multi-reflection system conceived by J. U. White and initially published in "Long Optical Paths of Large Aperture", Journal of the Optical Society of America, May 1942.

Figure 1:
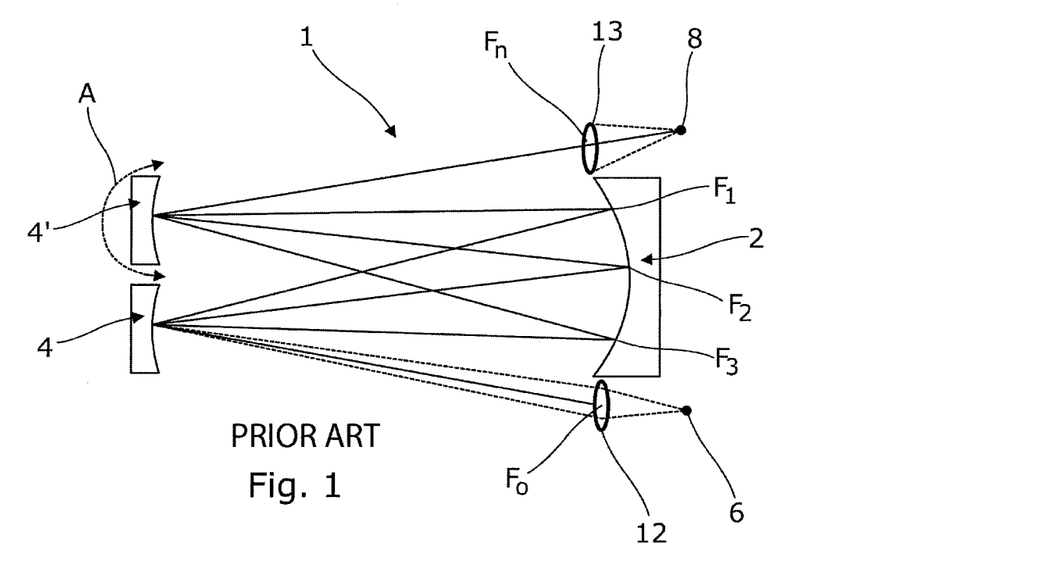
FIG. 1 is a schematic top view of a conventional White cell.
Figure 2:
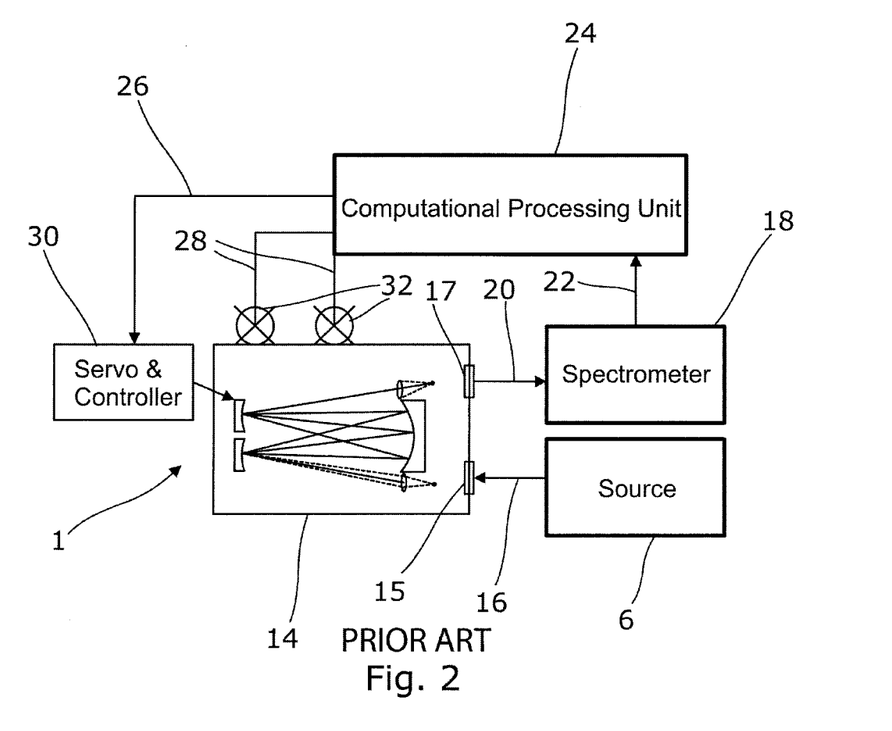
FIG. 2 is a schematic representation of a conventional optical absorption spectroscopy system.
Figure 3:
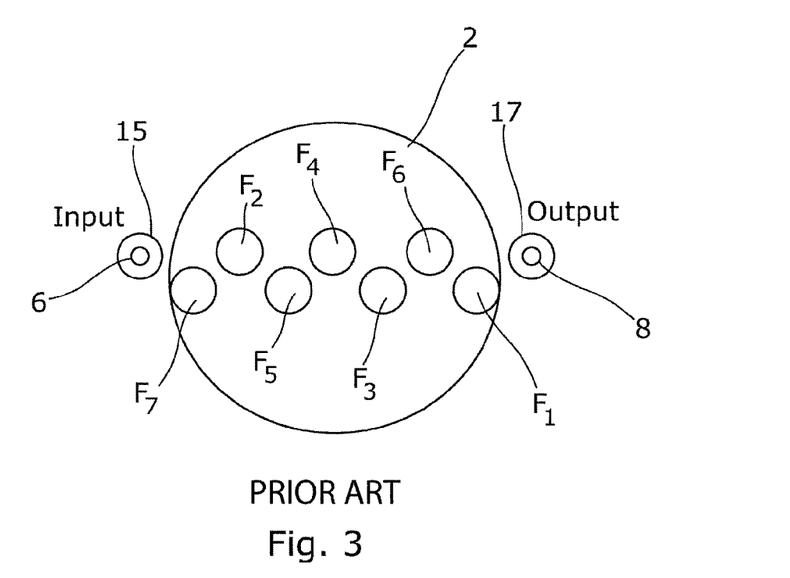
FIG. 3 illustrates the distribution of focal spots across the field mirror of a conventional White cell.

A typical White cell 1 consists of three concave mirrors 2, 4, 4' of identical radius of curvature, the basic configuration of which can be seen in FIGS. 1 to 3. The front (or field) mirror 2 faces the two side-by-side back (or objective) mirrors 4, 4', the distance between the two sets of mirrors being twice their focal length. Light from a source 6 at a point $F_0$ adjacent one edge of the front mirror is focused by the first back mirror 4 onto the surface of the front mirror 2 at point $F_1$. The front mirror 2 is oriented such that it reflects the light towards the second back mirror 4', which refocuses the light at point $F_2$ on the front mirror 2. This light is then refocused by the first back mirror 4 at point $F_3$, and so on thus forming a set of foci $F_1, F_2, F_3, \ldots$ across the surface of the front mirror 2. Eventually, after n passes, the light reflected by the second back mirror 4' falls off one side of the front mirror 2 at focal point $F_n$ and is collected by a detector 8. This light is then analysed by a spectrograph 10 to detect the optical absorption spectra of the substances through which the light has passed. In this example, the light source 6 and the detector 8 are each provided with a lens 12, 13 for focussing the light.

The second back mirror 4' can usually be rotated about its vertical axis as illustrated by arrow A in order to adjust how many times the light is reflected between the front and back mirrors before it falls off the side of the front mirror 2. This is referred to as "yaw adjustment". By adjusting the yaw, the pathlength of light through the sample can be controlled. One or both back mirrors 4, 4' may also be adjustable about a horizontal axis to adjust the plane in which the light is reflected. This is known as "pitch adjustment".

The White cell 1 is normally provided with a housing 14 as shown in FIG. 2, which contains the fluid sample. This housing 14 may be provided with entrance and exit windows 15, 17 for transmitting light to and from the cell 1.

In its most basic form, the light reflected within the White cell 1 stays entirely in one plane, which is referred to herein as the primary optical plane (this is commonly the horizontal plane). However, in practice the pitch of the two smaller objective mirrors 4, 4' is usually adjusted such that they are tilted in opposite directions in the vertical plane. The result of this is that the pattern on spots across the field mirror 2 is staggered across two separate rows as shown in FIG. 3. One of the rows has an even number of spots $F_1, F_3, F_5$, etc. and the other row has an odd number of spots $F_2, F_4, F_6$, etc. In this example the row with an odd number of spots is in the same plane as the entrance and exit windows 15, 17 and the source 6 and detector 8.

As will be apparent from the description above, the light from the source 6 is repeatedly refocused such that the effects of divergence over a long path length are minimised. Such divergent effects are typical from non-point sources of light and non-ideal collimation assemblies: this makes the White cell particularly useful for arc-based lamps. The White cell is the preferred multi-pass optical cell, although many practical alternatives exist such as Herriot cells, passive resonators, integrating spheres, etc.

Multi-pass optical cells are generally designed for use with electromagnetic radiation in a specific waveband, for example ultraviolet, visible or infrared. The chosen waveband dictates the choice of materials used for various optical components of the optical cell, such as the mirrors, entrance and exit windows and transmission optics (for example optical fibres). However, materials that are suitable for one waveband are often unsuitable for another waveband. For example, fused silica used as a window material is almost transparent to UV but virtually opaque to IR at certain wavelengths, whereas for a mirror material, silver has a high reflectance for visible and IR, but a very low reflectance at certain UV wavelengths. Therefore, multi-pass optical cells are generally designed for use with electromagnetic radiation in a specific waveband and cannot be used with radiation of other wavebands.

Of the various fluid substances that may be of interest, some may absorb significantly only in one waveband such as UV, whereas others may absorb significantly only in another waveband such as IR. If both types of substance are of interest, the inability of existing significant disadvantage. Yet other substances may absorb in both the UV and IR bands: in this case it may be beneficial to detect absorption in both bands for greater accuracy or sensitivity. However, this cannot be achieved with a conventional multi-pass cell.

U.S. Pat. No. 7,288,770 discloses a portable air monitoring system using UV spectroscopy capable of detecting chemicals in the open atmosphere or in a sample of air which is introduced into a chamber. The system enhances its sensitivity and accuracy by collecting a full spectrum of data points and by using multiple mirrors to increase the beam path in a closed-path length. The accuracy of these methods is good but not sufficient to fulfill the requirements that are present today, such as forming time-varying or real-time representative maps of pollution levels. Furthermore, this method does not allow for detection in multiple light wavebands.

U.S. Pat. No. 4,969,156 discloses a system including the adjustment of the second mirror to allow for calibration through overlapping laser pulses. The system does not provide for the determination of simultaneous absorptions across various frequencies.

U.S. Pat. No. 5,838,008 discloses the use of a White cell for the determination of gas concentrations via FTIR (Fourier transfer infrared spectroscopy). The method does not allow for the simultaneous detection of different wavebands of light.

SUMMARY

It is an object of the invention to mitigate at least one of the aforesaid disadvantages.

More specific preferred objects of the present invention are to provide an apparatus for optical absorption spectroscopy that permits the simultaneous or substantially simultaneous detection of optical absorption spectra in at least two different wavebands, and a method of optical absorption spectroscopy in which optical absorption spectra are detected in at least two different wavebands. Further objects of the invention are to provide apparatus and methods that mitigate at least some of the aforesaid disadvantages.

According to one aspect of the present invention there is provided an optical absorption spectroscopy apparatus comprising a multi-pass optical cell having a first reflector and a second reflector, a first light source for light of a first waveband and a second light source for light of a second waveband, the cell being constructed and arranged such that light entering the cell is reflected one or more times between the first and second reflectors before exiting the cell, and wherein light of the first waveband enters and exits the cell in a first plane P1, and light of the second waveband enters and exits the cell in a second plane P2 that is different from the first plane P1.

By providing different (i.e. not co-planar) entrance and exit planes for the two wavebands, it is possible to separate the two wavebands of light spatially from one another as they enter and leave the cell, and also as they pass through the cell. This permits the use of optical elements that are selected for their compatibility with the different wavebands of light. For example, different window materials may be used for the two wavebands, each material being transparent to the appropriate waveband. This allows the absorption characteristics of the sample fluid to be measured simultaneously in two different wavebands. Components of the sample fluid that absorb light in different wavebands can thus be detected simultaneously in a single instrument.

The different planes may for example be set at an acute angle to one another, so that they intersect at the location of the first reflector. In the case of a White cell, the first reflector comprises the objective mirrors. This allows for spatial separation of the two wavebands where they enter/exit the instrument, and also where they are reflected by the second reflector (the field mirror in a White cell). The two planes may be arranged so that they are both at an acute angle to the primary optical plane of the multi-pass cell, or so that one of those planes is at an acute angle to the primary optical plane and the other coincides with the primary optical plane. For the purposes of this document, the primary optical plane of a White cell is defined as being the plane that passes through the centres of the field mirror and the two objective mirrors. In practice, this is usually the horizontal plane.

Although the two wavebands of light enter the cell in different planes, the light paths of the two wavebands can if required be exactly equivalent in terms of number of passes through the cell and overall path length. This simplifies adjustment and operation of the apparatus. Alternatively, if required, different path lengths can be provided for each of the two wavebands by adjusting the direction of one or other of the incoming beams.

Advantageously, the apparatus includes a first entrance window for light of a first for light of the first waveband and a second exit window for light of the second waveband. Optionally, the first and second entrance windows may comprises different portions of a common entrance window and the first and second exit windows may comprises different portions of a common exit window. Preferably, the first entrance and exit windows lie in the first plane and the second entrance and exit windows lie in the second plane.

Preferably, the first entrance and exit windows are made of a first optical material that is substantially transparent to light of the first waveband, and the second entrance and exit windows are made of a second optical material that is substantially transparent to light of the second waveband.

The apparatus preferably includes a first detector for light of the first waveband and a second detector for light of the second waveband. The first and second detectors are preferably located in the first and second planes respectively.

The multi-pass cell preferably comprises a White cell having a front mirror and first and second back mirrors.

The apparatus preferably includes a measurement cell for containing a sample fluid. The apparatus may include means for transferring a sample fluid to and from the measurement cell. The apparatus is preferably constructed and arranged for analysing the optical absorption characteristics of a gas. Alternatively, it may be constructed and arranged for analysing the optical absorption characteristics of a liquid.

Preferably, the first waveband is ultraviolet and the second waveband is visible or infrared, or first waveband is ultraviolet or visible and the second waveband is infrared. More preferably, the first waveband is ultraviolet and the second waveband is infrared.

Advantageously, the first and second planes P1, P2 are arranged at an acute angle with respect to one another. For example, the planes P1, P2 may be arranged such that a L1 line normal to the first plane P1 and a line L2 normal to the second plane P2 lie in a common plane PC that coincides with a main optical axis of the multi-pass cell.

The first and second reflectors preferably comprise a material that is reflective to light of both the first waveband and the second waveband. The reflective material is preferably aluminium, which has a reflectance of greater than 80% for infrared, visible and ultraviolet light.

According to another aspect of the invention there is provided a method of measuring one or more components of a fluid, comprising placing a sample of the fluid in a multi-pass optical cell having a first reflector and a second reflector, passing light of a first waveband through the fluid and detecting the transmitted light; passing light of a second waveband through the fluid and detecting the transmitted light; wherein light of the first waveband enters and exits the cell in a first plane, and light of the second waveband enters and exits the cell in a second plane that is different from the first plane, and determining the concentration of one or more components of the fluid from the optical absorption spectra of the detected light.

Preferably, light of the first and second wavebands is passed simultaneously or substantially simultaneously through the fluid. The term "substantially simultaneously" is intended to encompass the possibility of passing the two wavebands through the cell in rapid succession as an alternative to actual simultaneity.

Preferably, the method includes passing the light through the fluid using a White cell.

The method preferably includes containing the fluid within a measurement cell.

In a preferred embodiment, the invention described herein couples ultraviolet and infrared light for the detection and quantification of gaseous (or liquid) species. The invention consists of a dual-White cell arrangement such that the optical geometry of the White cell is utilised to allow for combined input of both IR and UV into the same White cell IR and UV light enters/exits the White cell on separate optical planes, allowed for by staggering of beams within the White cell. This arrangement allows a more compact envelope for the instrument, lower costs because of shared components, simpler operation and manufacture and more powerful analysis owing to better control of systematic effects.

In multi-species fluid analysis, absorption of light can be used for the identification of fluid species, such as a pollution gas. This approach is strengthened if a number or a range of wavebands of light are considered. In the case of ultraviolet (UV) absorption, a number of species absorb typically through the excitation of outer-shell electrons and are therefore identifiable by measuring the quantity of light absorbed at wavelengths associated with those excitations. Not all gas species absorb strongly in the UV, but generally most do absorb in the infrared (IR) and near infrared (NIR) where typically interatomic vibrational excitations occur. Therefore a multi-species gas analyser ideally measures the absorption of light in both UV and NIR/IR.

The sensitivity of measurement achievable is partly governed by and roughly proportional to the path length of light absorbed through the gas and therefore it is desirable to have an arrangement such that a very long path length is achievable within the confines of a gas analyser. These so-called multi-pass arrangements can come in various forms. In a preferred embodiment, this invention is concerned primarily with one form of multipass cell, the White cell.

BRIEF DESCRIPTION OF THE DRAWINGS

An embodiment of the invention will now be described by way of example with reference to the accompanying drawings, wherein.

DETAILED DESCRIPTION

The basic White cell 1 consists of three concave mirrors 2, 4, 4' of identical radius of curvature, the basic configuration of which can be seen in FIG. 1. The mirrors comprise a large field mirror 2 that faces towards a pair of smaller objective mirrors 4, 4'.

Light from a source 6 is directed towards the first objective mirror 4 and is then reflected backwards and forwards a number of times between the mirrors. The light is continuously refocused so that the effects of divergence over a long path length are minimised. Such divergent effects are typical from non-point sources of light and non-ideal collimation assemblies, which makes the White cell particularly useful when the source 6 is an arc-based lamp. The White cell 1 is the preferred multi-pass optical cell, although many other types of multipass cell exist, such as Herriot cells, passive resonators, integrating spheres, etc.

Typically a White cell 1 comprises a large field mirror 2 and two smaller adjustable objective mirrors 4, 4' that are located some distance away. These objective mirrors 4, 4' optionally have adjustable pitch and yaw. Both the yaw and pitch are used to align the White cell to ensure that light reaches the detector 8 from the source 6. The yaw adjustment controls the direction of the light path in the lateral plane and the pitch adjustment controls the direction of the light path in the perpendicular plane (also referred to herein as the vertical plane).

A system for optical absorption spectroscopy is shown schematically in FIG. 2. This system includes a White cell 1 located within a measurement cell 14. Light from a light source 6 is transmitted to the White cell 1, for example via a first optical fibre or optical coupling 16, and detected light is transmitted to a spectrometer 18, for example by a second optical fibre or optical coupling 20. The output 22 of the spectrometer 18 is connected to a computational processing unit (CPU) 24 for analysis. The CPU 24 may also be connected, for example by wires 26, 28 to a servo and controller unit 30 for adjusting the yaw of the objective mirrors 4, 4' and to fans 32 for controlling the flow of sample fluids (e.g. gases) to and from the measurement cell 14.

In the application of ultraviolet (UV) spectroscopy, the broadband light passing through the cell is analysed for spectral absorption signatures. For limited amounts, the transmission of light is governed by the Beer-Lambert relationship wherein:

$$T(\lambda) = \frac{I(\lambda)}{I_0(\lambda)} = e^{-Lc\sigma(\lambda)}$$

Where $T(\lambda)$ is the fractional transmission with respect to wavelength $\lambda$, $I(\lambda)$ is intensity after passing through the fluid, $I_0(\lambda)$ is light entering the fluid, L is path length, c is the concentration of the absorbing fluid species (i.e. number density of molecules), and σ(λ) is the intrinsic absorption cross section of the fluid. Likewise $$D(\lambda) = \ln \frac{I(\lambda)}{I_0(\lambda)} = -Lc\sigma(\lambda)$$

in terms of absorbance, and in particular:

$$D'(\lambda) = \ln \frac{I(\lambda)}{I'_0(\lambda)} = -L\sum_{i=1}^{K} c_i \sigma'_i(\lambda)$$

when one or many (K) species absorb about a differential spectrum (i.e. one in which only features which vary rapidly with respect to wavelength are considered). $I'_0(\lambda)$ is the intensity in the absence of differential absorption which can be approximated numerically.

In its most basic form, a White cell can be described entirely in one plane (referred to herein as the horizontal plane). However, in practice the pitch of the two smaller objective mirrors is usually adjusted such that they are tilted in opposite directions in the vertical plane. The result of this is that the pattern on spots across the field mirror 2 is staggered across two separate rows, as shown in FIG. 3. Since there are always an odd number of spots in total, the number of spots in one of the rows is even and the number of spots in the other row is odd. In the embodiment of FIG. 3 the odd row is on the same plane as the input and output of light into the cell. The light source 6, the detector 8 and the entrance and exit windows 15, 17 are therefore located in this plane.

The use of UV and IR light poses some issues when being combined into a single gas cell. One of these is that in order to convey the light in and out of the cell (such as via a fibre optic), and to gas-seal the cell to be fluid-tight, windows need to be used. Finding a suitable material which conveys both IR and UV with high transmission is not possible. This issue is emphasised more where the combination is deep-UV and far-IR where suitable transmission materials are far apart.

Figure 6:
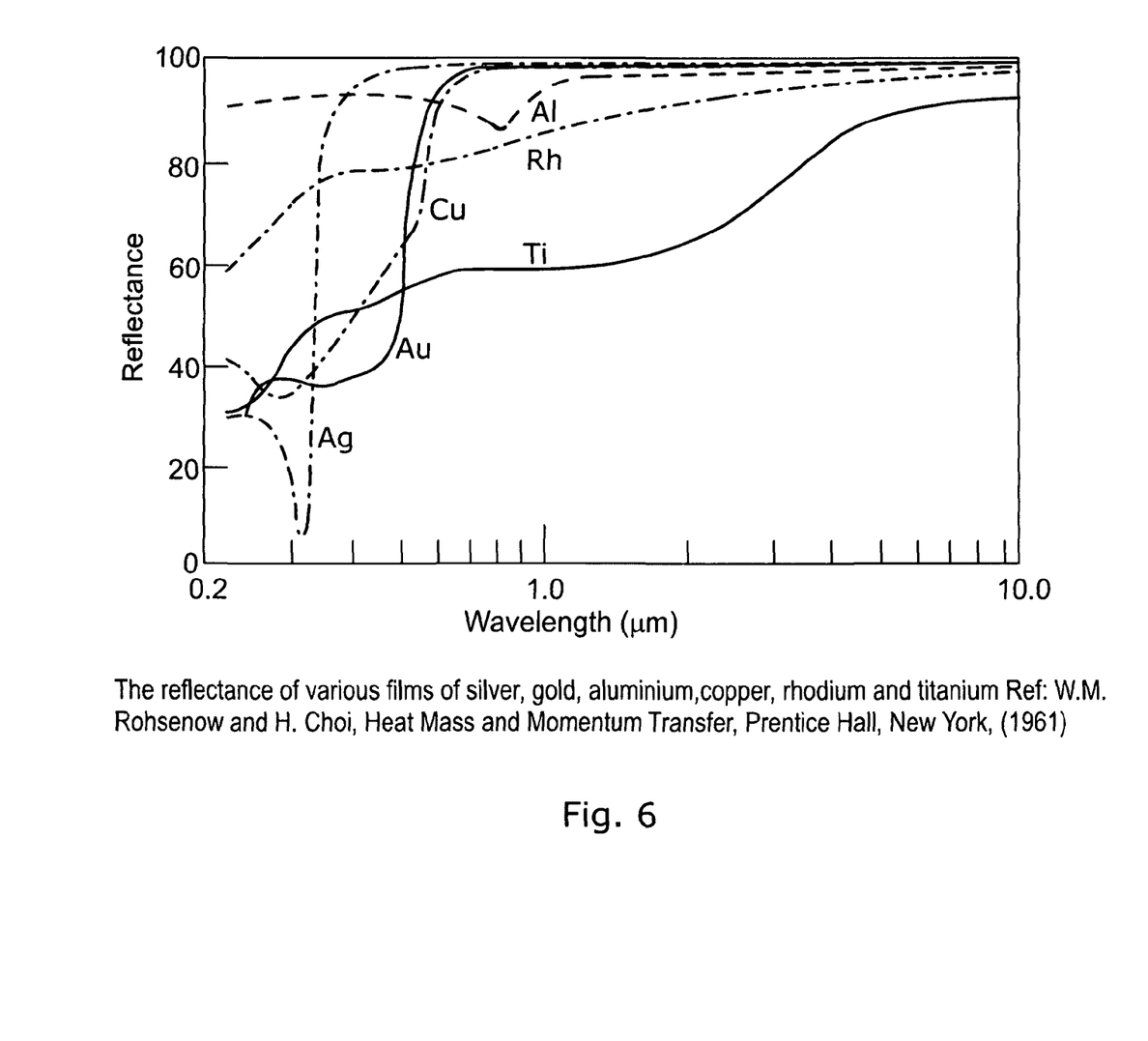
FIG. 6 is a graph representing the relationship between the reflectance of films of various materials and the wavelength of light in the ultraviolet, visible and infrared wavebands.

For the choice of mirror materials, aluminium coated mirrors are preferred as they have a reflectivity that is high enough to enable high throughput of light in the ultraviolet, visible and infrared wavebands through the cell, despite not having the highest reflectivity in the IR spectral region. This is illustrated in FIG. 6, which illustrates the reflectance of various films of silver, gold, aluminium, copper, rhodium and titanium at different wavelengths. It can be seen that the reflectance value stays above 80% in the ultraviolet (<0.38 μm), visible (0.38-0.75 μm) and infrared (<0.75 μm) wavebands. Furthermore there is evidence that aluminium mirrors are more robust to corrosive environments where certain gases are being analysed.

Figure 4:
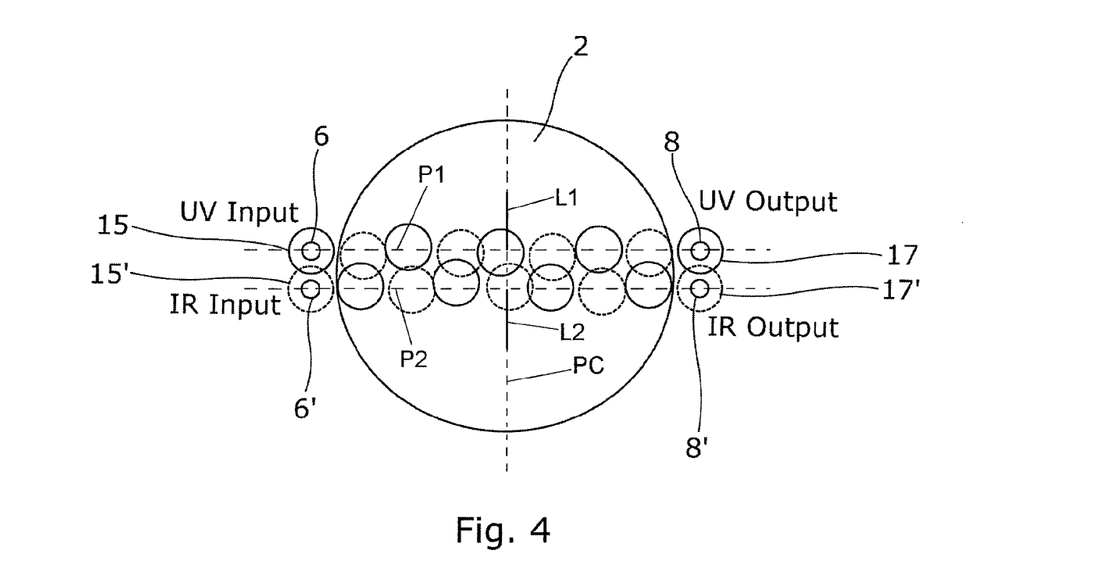
FIG. 4 illustrates the distribution of focal spots across the field mirror of a multipass optical absorption cell according to an embodiment of the present invention.

The embodiment of the invention disclosed here consists of a White cell in which light in two wavebands is staggered in two planes P1, P2. Since the positional adjustment of the mirror assembly is consistent with two planes for one White cell, an inverted set of planes can be utilised such that they are fully coincident with the first. This is illustrated in FIG. 4, which shows a pattern of spots spread across the field mirror 2. In this example there are two separate sets of spots, spots of UV light being shown as solid circles and spots of IR light being shown as broken circles. Each of these sets of spots is staggered across two separate rows, the spots of one waveband being located between the spots of the other waveband.

It can be seen how light in the UV waveband enters and exits the cell in one plane P1 through a first pair of entrance and exit windows 15, 17 while light in the IR waveband enters and exits the cell in another plane P2 through a second pair of entrance and exit windows 15', 17'. This makes it possible to locate the sources 6, 6' and the detectors 8, 8' side-by-side without overlap.

Figure 5:
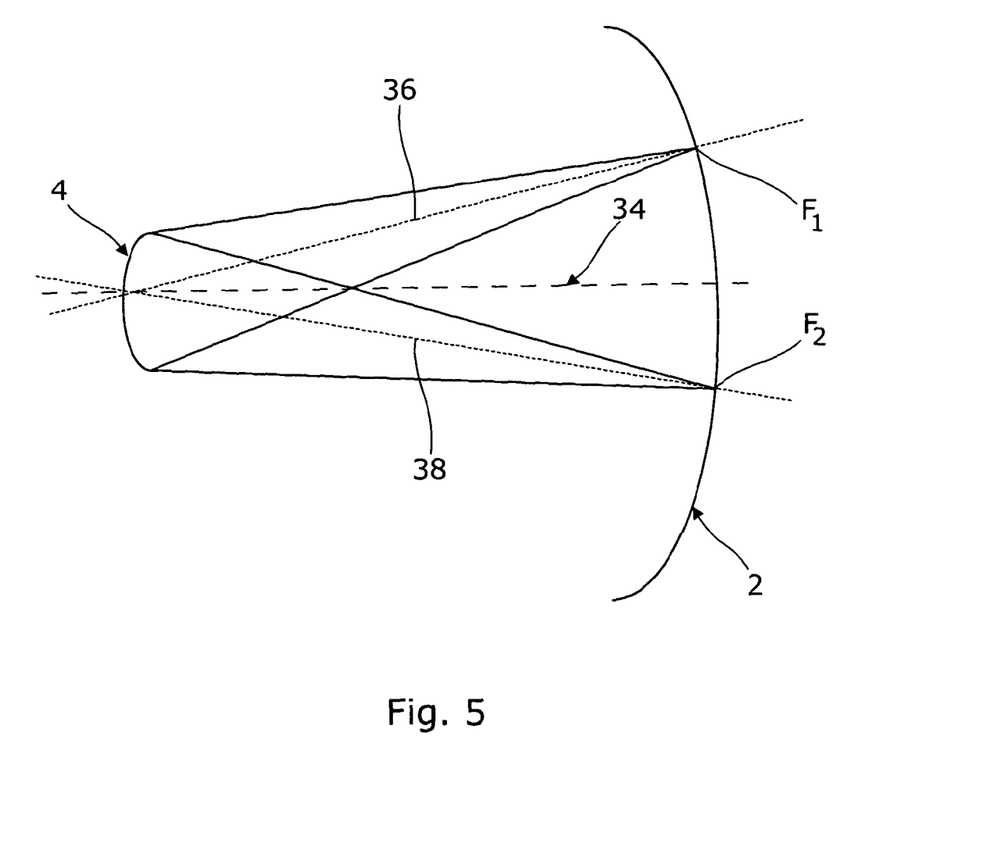
FIG. 5 is a side view of a multipass optical absorption cell according to the present invention.

This dual White cell arrangement is made by inputting light into the cell at a pitched angle to the horizontal plane. FIG. 5 illustrates this. Light from a first focal point $F_1$ on the field mirror 2 is reflected by the objective mirror 4 to a second focal point $F_2$ on the field mirror 2. The first focal point $F_1$ is located above the primary optical plane 34 and the second focal point $F_2$ is located below the primary optical plane 34. The entrance and exit windows for each waveband may be located either in the top plane 36 or the bottom plane 38. Given that each input/output needs to be coincident with one of the two planes 36, 38 in order for the White cell to operate, the input/output light sources need to be carefully arranged. We herein refer to these planes as top and bottom, and the rows on the field mirror also as top and bottom.

For ease of manufacture and assembly, it is desirable to choose either the top plane 36 or the bottom plane 38 to be coincident with the horizontal primary optical plane 34. Additionally, where the dimensions of either of the sources or either of the detectors are so large as to prevent them being placed in close proximity to each other to fit the dual-White cell arrangement, transfer mirrors or other transfer optics may be used for input/output to either of the two planes. This method also allows for easier directional adjustment as the light enters and exits the cell, and therefore is suitable for the plane that is not coincident with the primary optical plane. The field mirror 2 can be positioned such that both the top and bottom rows of spots extend over equally wide regions of the mirror.

The yaw of the two small objective mirrors 4, 4' sets the number of passes of light through the White cell and as such, it is convenient to require the IR part of the White cell must have the same number of passes as the UV part.

Figure 7:
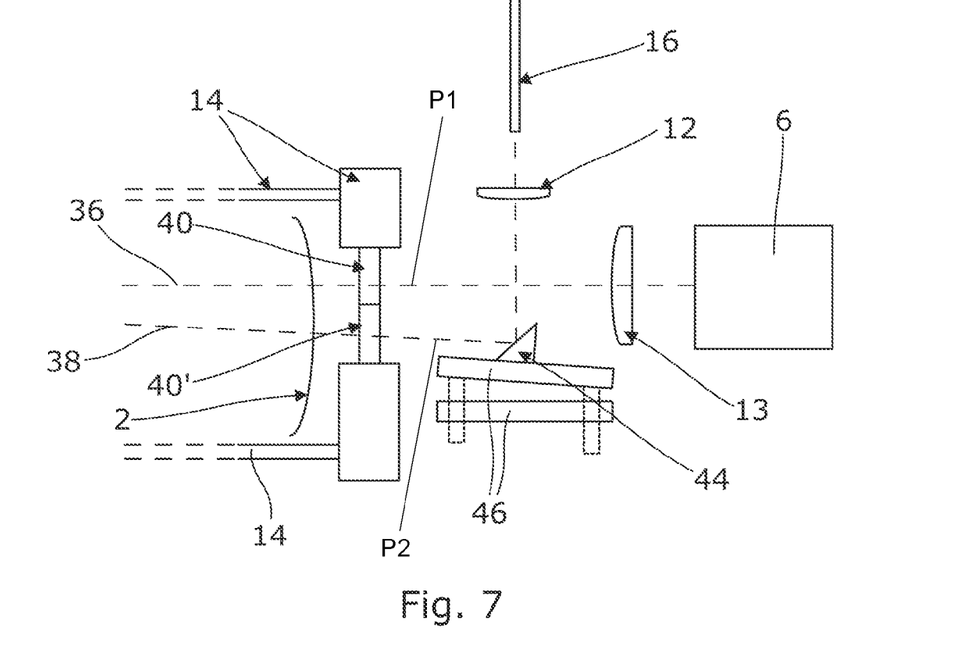
FIG. 7 is a side view showing one end of a multipass optical absorption cell according to the present invention.

FIG. 7 illustrates an optical arrangement that allows for the alignment of UV and IR in the vertical plane such that each waveband enters the cell in a separate plane P1, P2. In this drawing, only the input/output end of the White cell 1 is shown, which contains the field mirror 2. The White cell 1 includes a measurement cell 14 and in the end of the cell there is provided a first entrance window 40 for UV light and a second entrance window 40' for IR light. The White cell also includes a matching pair of exit windows 42, 42' but these cannot be seen in FIG. 7 as they are located directly behind the entrance windows 40, 40'. Similarly, the detectors 8, 8' for the UV and IR light are hidden behind the UV and IR sources 6, 6'.

In this embodiment, the UV source 6 is aligned with the top plane 36, P1 and transmits a beam of UV light into the White cell through the UV entrance window 40, via a collimator lens 13. The IR source 6' (not shown) is located remotely and IR light is transmitted to the White cell, preferably via an IR fibre optic 16, or IR focusing assembly to provide a divergent beam into the White cell. A beam of IR light is transmitted into the White cell 1 along the bottom plane 38, P2 through the IR entrance window 40', via a lens 12 and an IR transfer mirror 44. The IR transfer mirror 44 is mounted on an adjustment stage 46, which allows the position of the bottom plane 38 to be adjusted. The transfer mirror 44 may be oriented such that the beam can enter from the side, above, or below the White cell. A similar arrangement is located at the exit, where both IR and UV are beams collected and analysed, typically into a waveband-specific detector (e.g. UV-Vis spectrometer and FTIR spectrometer).

Figure 9A:
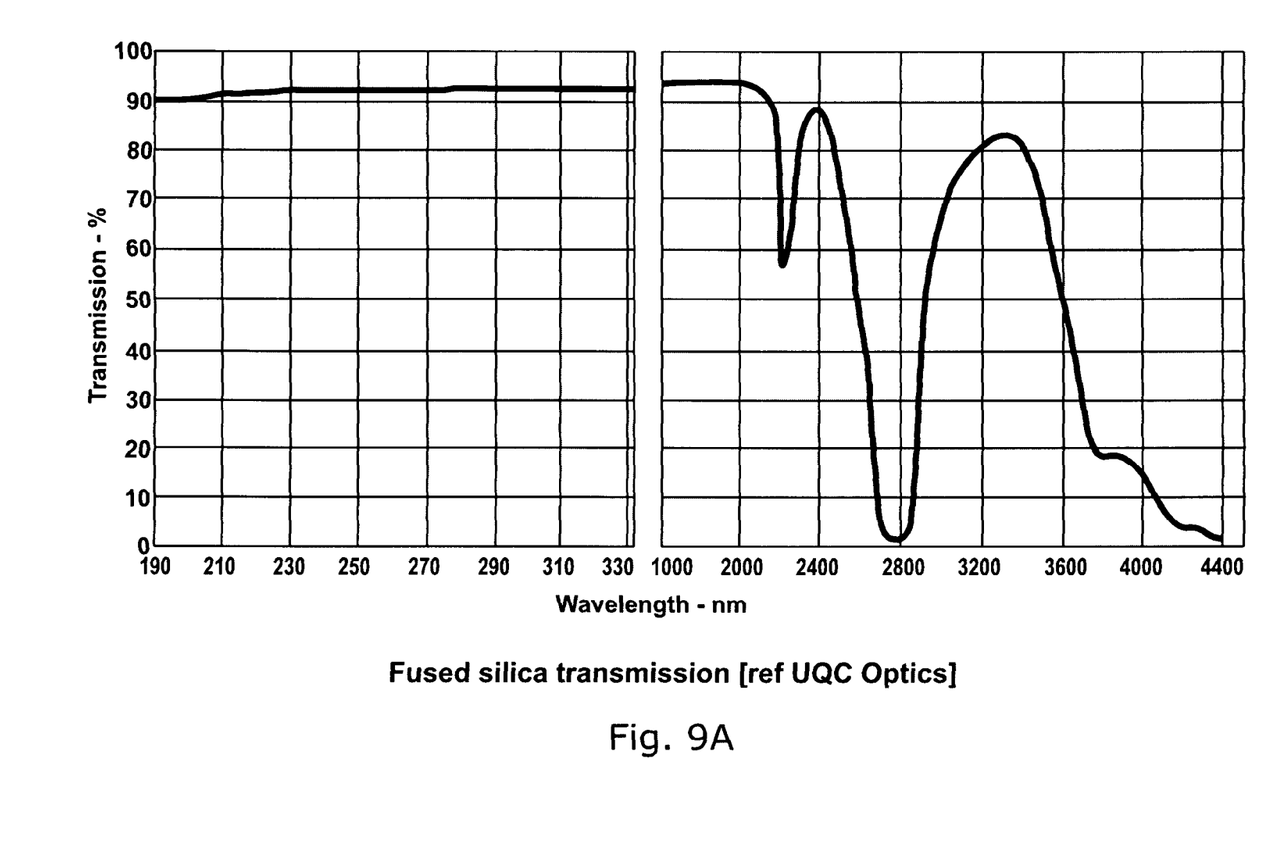
FIG. 9A is a graph representing the transmission characteristics of fused silica to light in the ultraviolet and infrared wavebands.
Figure 9B:
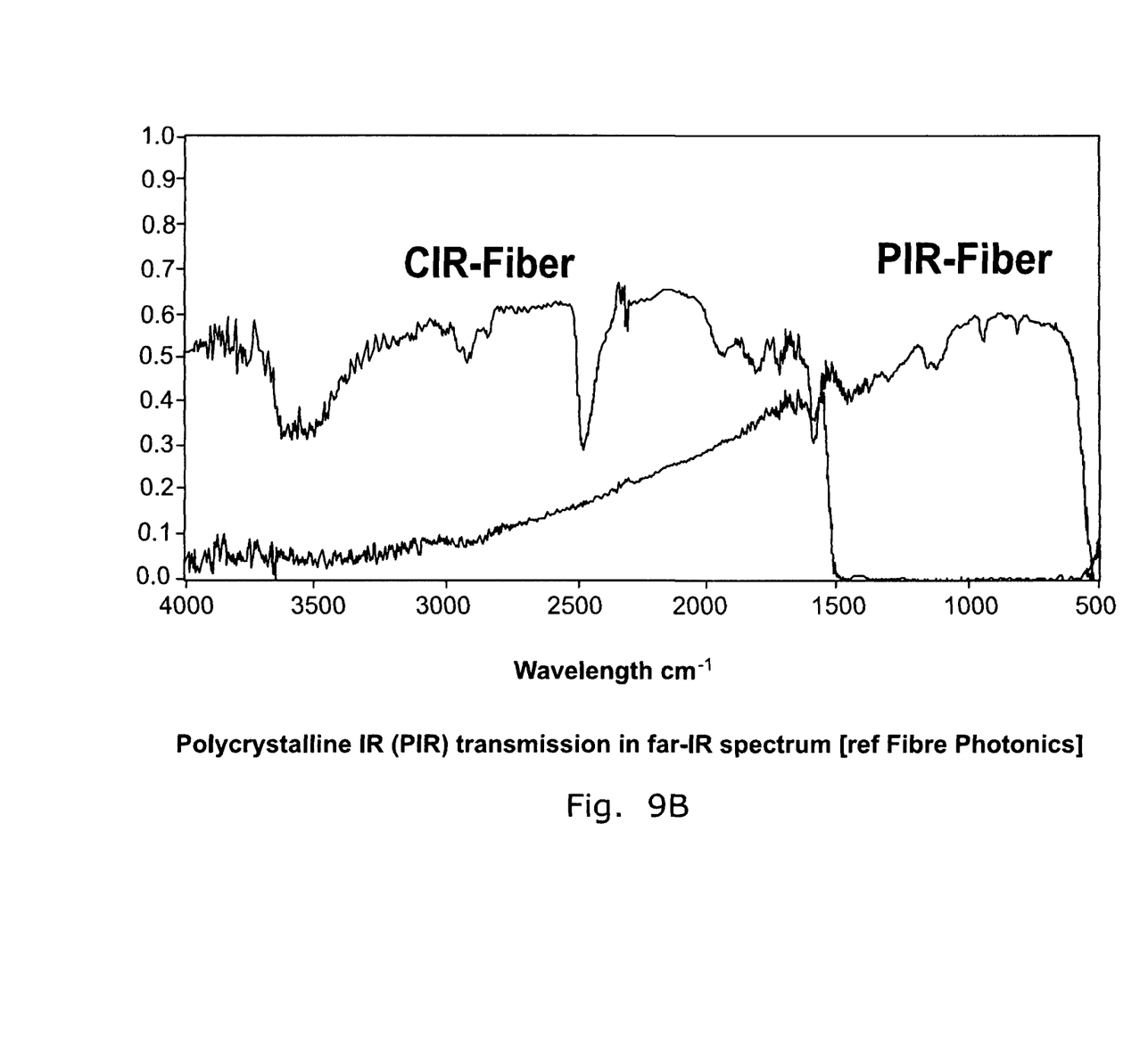
FIG. 9B is a graph representing the transmission characteristics of CIR-Fibre and PIR-Fibre to light in the mid and far infrared waveband.

The entrance windows 40, 40' and the exit windows 42, 42' are each made of a material having high transmission characteristics for the chosen waveband. Thus, the UV windows may be made for example of fused silica, which has high transmission characteristics for UV light but low transmission characteristics for much of the IR waveband, as illustrated in FIG. 9a. Conversely, the IR windows may be made for example of chalcogenide IR glass (CIR) or polycrystalline alumina (PIR), which have high transmission characteristics for light in the mid-IR and far IR waveband, as illustrated in FIG. 9b.

Figure 8:
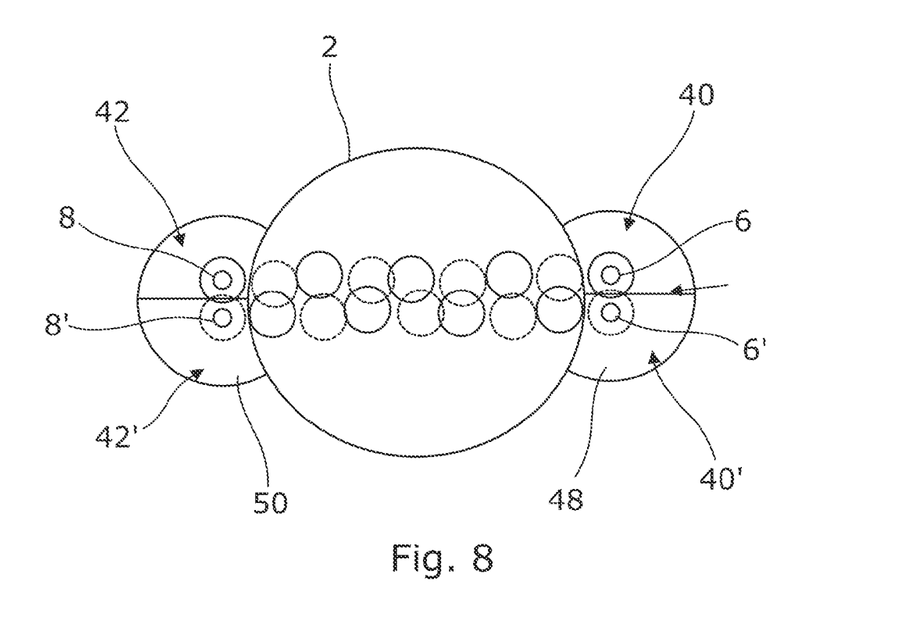
FIG. 8 illustrates the arrangement of the field mirror and the entrance/exit windows in a multipass optical absorption cell according to an embodiment of the present invention.

FIG. 8 illustrates the beam pattern with separate entrance windows 40, 40' and exit windows 42, 42' behind the main field mirror 2. In this example, the two entrance windows 40, 40' are formed within a single window aperture 48, and thus consist of separate window portions. The different window materials are bonded to one another with a suitable adhesive to form a gas-tight seal. Likewise, the two exit windows 42, 42' are formed within a single window aperture 50. The UV and IR sources 6, 6' are located behind the entrance windows 40, 40' and the UV and IR detectors' entry points 8, 8' are located behind the exit windows 42, 42'.

In the analysis stage, certain gases have signatures in both the UV and IR, such as ammonia. In these circumstances, it is desirable to correlate the determination of species concentration through numerical analysis. The level of certainty with which these gases can be determined in both spectral ranges can be numerically coupled such that the concentrations can be combined in weighted proportion with the level of certainty. In this process the overall level of uncertainty in gas concentration determination can be minimised by combination of errors in proportion.

The invention claimed is:

1. An optical absorption spectroscopy apparatus comprising a multi-pass optical cell comprising a first reflector and a second reflector, a first light source for light of a first waveband and a second light source for light of a second waveband that is different from the first waveband, the cell being constructed and arranged such that light entering the cell is reflected one or more times between the first and second reflectors before exiting the cell, and wherein light of the first waveband comprises a first input beam that enters the cell and a first output beam that exits the cell, wherein the first input beam and the first output beam lie in a first plane, and light of the second waveband comprises a second input beam that enters the cell and a second output beam that exits the cell, wherein the second input beam and the second output beam lie in a second plane that is different from the first plane, and wherein a line normal to the first plane and a line normal to the second plane lie in a common plane that coincides with a main optical axis of the multi-pass cell.

2. An apparatus according to claim 1, including a first entrance window for light of a first waveband, a second entrance window for light of a second waveband, a first exit window for light of the first waveband and a second exit window for light of the second waveband.

3. An apparatus according to claim 2, wherein the first entrance and exit windows lie in the first plane and the second entrance and exit windows lie in the second plane.

4. An apparatus according to claim 2, wherein the first entrance and exit windows are made of a first optical material that is substantially transparent to light of the first waveband, and the second entrance and exit windows are made of a second optical material that is substantially transparent to light of the second waveband.

5. An apparatus according to claim 1, further including a first detector for light of the first waveband and a second detector for light of the second waveband.

6. An apparatus according to claim 1, wherein the multi-pass cell comprises a White cell having a front mirror and first and second back mirrors.

7. An apparatus according to claim 1, further including a measurement cell for containing a sample fluid.

8. An apparatus according to claim 7, further including means for transferring a sample fluid to and from the measurement cell.

9. An apparatus according to claim 1, wherein the apparatus is constructed and arranged for analysing the optical absorption characteristics of a gas.

10. An apparatus according to claim 1, wherein the first waveband is ultraviolet and the second waveband is visible or infrared.

11. An apparatus according to claim 10, wherein the first waveband is ultraviolet and the second waveband is infrared.

12. An apparatus according to claim 1, wherein the first and second reflectors comprise a material that is reflective to light of both the first waveband and the second waveband.

13. An apparatus according to claim 12, wherein the reflective material is aluminium.

14. An apparatus according to claim 1, wherein the first waveband is ultraviolet or visible and the second waveband is infrared.

15. A method of measuring one or more components of a fluid, comprising:
   a. placing a sample of the fluid in a multi-pass optical cell having a first reflector and a second reflector,
   b. passing light of a first waveband through the fluid and detecting the transmitted light;
   c. passing light of a second waveband through the fluid and detecting the transmitted light, wherein the second waveband is different from the first waveband;
   d. wherein light of the first waveband comprises a first input beam that enters the cell and a first output beam that exits the cell, wherein the first input beam and the first output beam lie in a first plane, and light of the second waveband comprises a second input beam that enters the cell and a second output beam that exits the cell, wherein the second input beam and the second output beam lie in a second plane that is different from the first plane, and wherein a line normal to the first plane and a line normal to the second plane lie in a common plane that coincides with a main optical axis of the multi-pass cell, and
   e. determining the concentration of one or more components of the fluid from the optical absorption spectra of the detected light.

16. A method according to claim 15, in which light of the first and second wavebands is passed substantially simultaneously through the fluid.

17. A method according to claim 15, including passing the light through the fluid using a White cell.

18. A method according to claim 15, further including containing the fluid within a measurement cell.

19. An optical absorption spectroscopy apparatus comprising a multi-pass optical cell comprising a first reflector and a second reflector, a first light source for light of a first waveband, a first entrance window for light of the first waveband, a first exit window for light of the first waveband, a second light source for light of a second waveband, a second entrance window for light of the second waveband and a second exit window for light of the second waveband, the cell being constructed and arranged such that light entering the cell is reflected one or more times between the first and second reflectors before exiting the cell, and wherein light of the first waveband enters and exits the cell in a first plane, and light of the second waveband enters and exits the cell in a second plane that is different from the first plane, and wherein a line normal to the first plane and a line normal to the second plane lie in a common plane that coincides with a main optical axis of the multi-pass cell.

* * * * *

UNITED STATES PATENT AND TRADEMARK OFFICE
CERTIFICATE OF CORRECTION

PATENT NO. : 9,194,794 B2
APPLICATION NO. : 13/700633
DATED : November 24, 2015
INVENTOR(S) : Steven Wilkins Page 1 of 1

It is certified that error appears in the above-identified patent and that said Letters Patent is hereby corrected as shown below:

In the specification

Please replace the paragraph starting at column 2, line 55, with the following paragraph:

Of the various fluid substances that may be of interest, some may absorb significantly only in one waveband such as UV, whereas others may absorb significantly only in another waveband such as IR. If both types of substance are of interest, the inability of existing multi-pass optical cells to detect absorption in more than one specific waveband presents a significant disadvantage. Yet other substances may absorb in both the UV and IR bands: in this case it may be beneficial to detect absorption in both bands for greater accuracy or sensitivity. However, this cannot be achieved with a conventional multi-pass cell.

Please replace the paragraph starting at column 4, line 14, with the following paragraph:

Advantageously, the apparatus includes a first entrance window for light of a first waveband, a second entrance window for a light of a second waveband, and a first exit window for light of the first waveband and a second exit window for light of the second waveband. Optionally, the first and second entrance windows may comprise different portions of a common entrance window and the first and second exit windows may comprise different portions of a common exit window. Preferably, the first entrance and exit windows lie in the first plane and the second entrance and exit windows lie in the second plane.

Signed and Sealed this
Nineteenth Day of April, 2016

Michelle K. Lee
*Director of the United States Patent and Trademark Office*